United States Patent
Einarsson et al.

(10) Patent No.: US 9,112,933 B2
(45) Date of Patent: Aug. 18, 2015

(54) METHOD AND ARRANGEMENT FOR ADAPTION IN HTTP STREAMING

(75) Inventors: Torbjörn Einarsson, Stockholm (SE); Per Fröjdh, Stockholm (SE); Clinton Priddle, Indooroopilly (AU); Zhuangfei Wu, Danderyd (SE)

(73) Assignee: TELEFONAKTIEBOLAGET L M ERICSSON (PUBL), Stockholm (SE)

( * ) Notice: Subject to any disclaimer, the term of this patent is extended or adjusted under 35 U.S.C. 154(b) by 113 days.

(21) Appl. No.: 13/579,205

(22) PCT Filed: Feb. 16, 2011

(86) PCT No.: PCT/SE2011/050167
§ 371 (c)(1),
(2), (4) Date: Aug. 15, 2012

(87) PCT Pub. No.: WO2011/102792
PCT Pub. Date: Aug. 25, 2011

(65) Prior Publication Data
US 2012/0317189 A1 Dec. 13, 2012

Related U.S. Application Data

(60) Provisional application No. 61/305,983, filed on Feb. 19, 2010.

(51) Int. Cl.
*H04L 29/06* (2006.01)
*H04L 29/08* (2006.01)

(52) U.S. Cl.
CPC .......... *H04L 65/4084* (2013.01); *H04L 65/607* (2013.01); *H04L 65/80* (2013.01); *H04L 67/02* (2013.01)

(58) Field of Classification Search
CPC ............................ H04L 65/608; H04L 65/607
USPC ................................................ 709/203, 246
See application file for complete search history.

(56) References Cited

U.S. PATENT DOCUMENTS

2003/0025832 A1* 2/2003 Swart et al. ................... 348/461
2007/0169152 A1* 7/2007 Roodnick et al. ............... 725/62
(Continued)

FOREIGN PATENT DOCUMENTS

JP 2007036666 A 2/2007
JP 2008236390 A 10/2008
(Continued)

OTHER PUBLICATIONS

Realnetworks Inc., et al., "Format for HTTP Streaming Media Presentation Description," 3GPP SA4-MBS SWG on MBS_Ext, Jan. 25-29, 2010, St. Julian, Malta, Tdoc S4-100020.
"Segment Alignment and related issues in HTTP Streaming." TSG-SA4#6-SWG on HTTP Streaming, Tdoc S4 AH1151, Aachen, Germany, Mar. 2-4, 2010.
(Continued)

*Primary Examiner* — Brian J Gillis
*Assistant Examiner* — Steve Lin
(74) *Attorney, Agent, or Firm* — Coats & Bennett, PLLC (57) ABSTRACT

A method of controlling adaptive HTTP streaming of media content between a HTTP server and a HTTP client in a communication system, in which system media content is arranged as a plurality of periods, and each such period comprises a plurality of representations of media segments, which method includes the steps of providing (S10) temporal alignment information for the media segments of the plurality of representations, which temporal alignment information provides indications about a temporal relation between the segments of the plurality of representations of the media content. Further, the method includes providing (S20) key frame location information for the media segments, which key frame location information provides indications about locations of key frames in the media segments of the plurality of representations. Finally, controlling (S30) adaptation of the HTTP streaming of the media content based on at least one of the provided temporal alignment information and the provided key frame location information.

19 Claims, 10 Drawing Sheets

(56) References Cited

U.S. PATENT DOCUMENTS

| | | | |
|---|---|---|---|
| 2009/0115901 A1 | 5/2009 | Winter et al. | |
| 2009/0150557 A1* | 6/2009 | Wormley et al. | 709/231 |
| 2009/0199248 A1* | 8/2009 | Ngo et al. | 725/90 |
| 2009/0282162 A1* | 11/2009 | Mehrotra et al. | 709/233 |
| 2011/0099594 A1* | 4/2011 | Chen et al. | 725/105 |
| 2011/0169963 A1* | 7/2011 | Winkler | 348/180 |
| 2011/0268178 A1* | 11/2011 | Park et al. | 375/240.02 |
| 2012/0233345 A1 | 9/2012 | Hannukela | |

FOREIGN PATENT DOCUMENTS

| | | |
|---|---|---|
| JP | 2009502067 A | 1/2009 |
| WO | 2009154529 A1 | 12/2009 |

OTHER PUBLICATIONS

3rd Generation Partnership Project. "Fragmented Time Indexing of Representations." 3GPP TSF-SA4 Ad-Hoc Meeting, S4AHI126, Paris, France, Dec. 14-16, 2009.

3rd Generation Partnership Project. "Pseudo CR: Adaptive HTTP Streaming in PSS—Data Formats for HTTP-Streaming excluding MPD." 3GPP TSG-AHI Meeting #nn, S4-AHI128, Paris, France, Dec. 13-15, 2009.

3rd Generation Partnership Project. "Pseudo CR: Adaptive HTTP Streaming in PSS—Client Behaviour." 3GPP TSG-AHI Meeting #nn, S4-AHI129, Paris, France, Dec. 13-15, 2009.

3rd Generation Partnership Project. "Adaptive HTTP Streaming in PSS—Discussion on Options." 3GPP TSG-SA4 AHI Meeting, S4-AHI0130, Paris, France, Dec. 14-16, 2009.

* cited by examiner

Fig. 7

METHOD AND ARRANGEMENT FOR ADAPTION IN HTTP STREAMING

TECHNICAL FIELD

The present disclosure concerns communication systems in general, specifically adaptation during HTTP streaming sessions in such systems.

BACKGROUND

There is an increased interest in HTTP (Hyper Text Transfer Protocol) streaming of media, in particular video. Recently, this has evolved beyond simple progressive download to give two new features: adaptivity and live content. The way this is achieved is that the content is partitioned into multiple segments, or files, each corresponding to a small interval of content, for example 10 seconds of content. The client is provided with a manifest file, also known as a Media Presentation Description, (MPD), which lists the different segments and where to fetch them and the client fetches them one by one. The split into different segments/files that are fetched via a standard web protocol e.g. HTTP, is also said to be cache-friendly, or CDN (Content Distribution Network) friendly, since it does not require any state in the server or cache, in contrast with streaming servers based on protocol such as RTSP (Real Time Streaming Protocol). Multiple levels are possible within intervals and segments. For example, it is possible to do add insertion, by changing the content during one interval, and then return to the original content stream in the next interval.

Adaptivity is achieved by providing multiple versions of the content, so that the client can chose to fetch the version which it estimates to be the best given the network performance/download time. From the clients' point of view, adaptivity is much easier solved if the segments of different versions or representations have the same duration, so that the client can simply make the decision for each segment download on which version to chose. However, by imposing the same duration for all versions of the segments, their respective sizes will vary significantly. This is by no means optimal for the caching servers, which often have better performance if the segments are of the same, or similar, size. Size-alignment is therefore desirable for the caches/servers, but makes the adaptivity mechanism in the clients more difficult. Whether one should optimize for the servers or the clients is a tradeoff.

Two existing solutions to this problem are SmoothStreaming from Microsoft® and LiveStreaming from Apple®, both of which have chosen the equal duration track. Within 3GPP SA4 the discussions mainly deal with equal size tracks instead.

Based on the above, there is a need for a solution that allows for different trade-offs between adaptivity performance on the client side and equal-size files/segments on the servers/caches.

SUMMARY

It is an object to obviate at least some of the above disadvantages and provide improved adaptive HTTP media streaming control.

According to a first aspect, the present disclosure presents a method of controlling adaptive HTTP streaming of media content between a HTTP server and a HTTP client in a communication system, which media content is arranged as a plurality of periods, and each such period comprises a plurality of representations of media segments. The method includes the steps of providing temporal alignment information for the media segments of the plurality of representations, which temporal alignment information provides indications about a temporal relation between the segments of the plurality of representations of the media content. Further, the method includes the step of providing key frame location information for the media segments, which key frame location information provides indications about locations of key frames in the media segments of the plurality of representations. Finally, the method includes the step of controlling adaptation of the HTTP streaming of the media content based on at least one of the provided temporal alignment information and the provided key frame location information.

According to a second aspect, the present disclosure presents a method for use in a HTTP server node for streaming of media content to a HTTP client in a communication system, which media content is arranged as a plurality of periods, and each such period comprises a plurality of representations of media segments. The method includes the step of providing temporal alignment information for the media segments of the plurality of representations, which temporal alignment information provides indications about a temporal relation between the segments of the plurality of representations of the media content. Further the method includes the step of providing key frame location information for the media segments, which key frame location information provides indications about locations of key frames in the media segments of the plurality of representations.

According to a third aspect, the present disclosure presents a method for use in a HTTP client node for receiving streaming media content from a HTTP server node in a communication system, which media content is arranged as a plurality of periods, and each such period comprises a plurality of representations of media segments. The method includes the step of receiving temporal alignment information for the media segments of the plurality of representations, which temporal alignment information provides indications about a temporal relation between the segments of the plurality of representations of the media content. Further, the method includes the step of receiving key frame location information for the media segments, which key frame location information provides indications about locations of key frames in the media segments of the plurality of representations. Finally, the method includes the step of controlling adaptation of the HTTP streaming of the media content based on at least one of the received temporal alignment information and the received key frame location information.

According to a fourth aspect, the present disclosure presents a HTTP server node for streaming of media content to a HTTP client in a communication system, which media content is arranged as a plurality of periods, and each such period comprises a plurality of representations of media segments. The server node includes a temporal alignment information provider configured to provide temporal alignment information for the media segments of the plurality of representations, which temporal alignment information provides indications about a temporal relation between the segments of the plurality of representations of the media content. In addition, the server node includes a key frame location provider configured to provide key frame location information for the media segments, which key frame location information provides indications about locations of key frames in the media segments of the plurality of representations.

According to a fifth aspect, the present disclosure a HTTP client node for receiving streaming of media content from a HTTP server node, which media content is arranged as a plurality of periods, and each such period comprises a plurality of representations of media segments. The client node includes a temporal alignment information receiver configured for receiving temporal alignment information for the media segments of the plurality of representations, which temporal alignment information provides indications about a temporal relation between the segments of the plurality of representations of the media content. Further, the client node includes a key frame location receiver configured to receive key frame location information for the media segments, which key frame location information provides indications about locations of key frames in the media segments of the plurality of representations. Finally, the client node includes an adaptation controller configured for controlling adaptation of the HTTP streaming of the media content based on at least one of the received temporal alignment information and the received key frame location information.

Advantages of the present disclosure includes enabling improved control of adaptation during HTTP streaming sessions.

BRIEF DESCRIPTION OF THE DRAWINGS

The invention, together with further objects and advantages thereof, may best be understood by making reference to the following description taken together with the accompanying drawings, in which:

FIG. 5A-E are schematic illustrations embodiments of the present disclosure FIG. 6A-D are schematic illustrations embodiments of the present disclosure

ABBREVIATIONS

HTTP Hyper Text Transfer Protocol
GOP Group Of Pictures
RAP Random Access Point (key frame)
MPD Media Presentation Description
CDN Content Distribution Network
RTSP Real Time Streaming Protocol

DETAILED DESCRIPTION

Throughout the drawings, the same reference numbers are used for similar or corresponding elements.

As discussed in the background section, there is in present HTTP streaming systems a need to balance the trade-offs between adaptivity performance on the client side and equal-size files/segments on the servers/caches. The inventors have come to the realization that it would be beneficial to allow non-equal size segments if it was possible to indicate to the client node about the relationship between the various segments and representations. By providing a solution where information about a present state of segmentation, such as temporal alignment between one or more segments in one or more representations, a client could perform adaptation based on that information to the benefit of both client and server node.

As identified by the inventors, it would be beneficial to signal in the aforementioned manifest whether all versions or representations of a segment have aligning borders or not. This can for example be done using a flag, equalSegmentVersionDurations when all representations start at the same time (as given these two constraints, alignment occurs). Since segment alignment makes adaptivity simpler, the client can then choose to only provide adaptivity in case this flag signals segment alignment. In case the flag is not set, duration needs to be provided for each of the versions of the segments, which if it is set, only duration is needed that applies to all versions. Although most of the present disclosure describes signaling in the manifest, it is equally possible to signal the temporal alignment information in some other manner.

Figure 1:
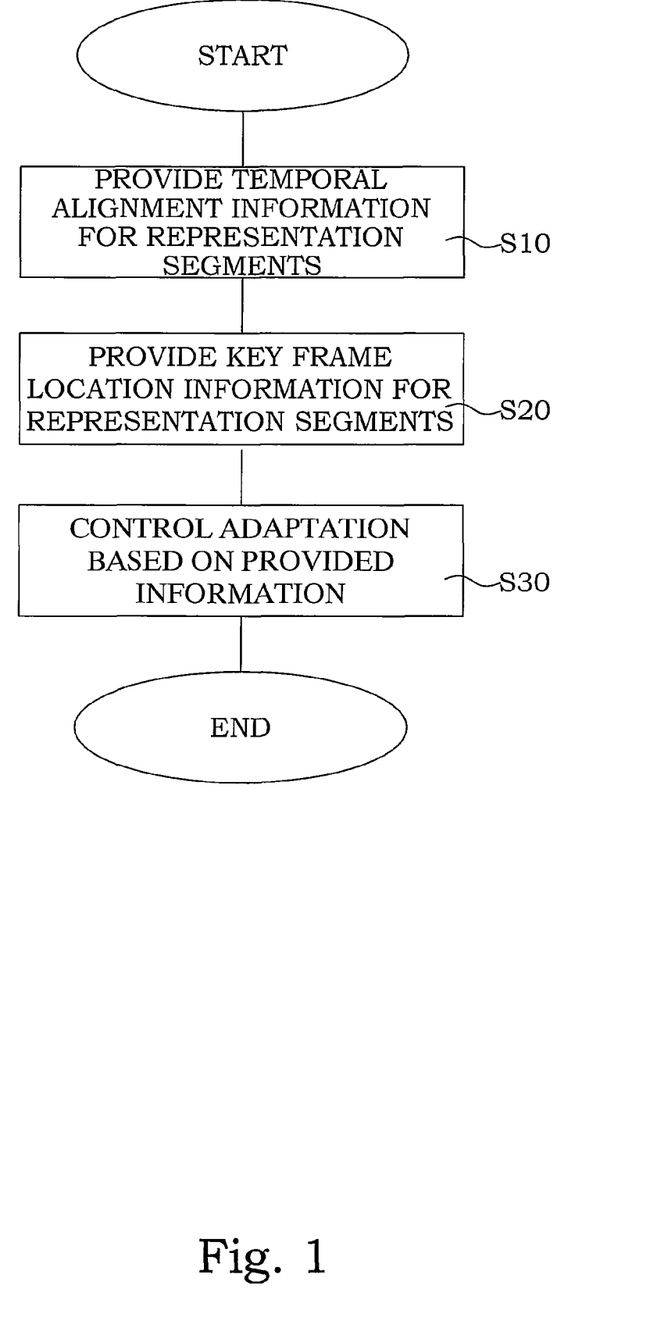
FIG. 1 is a schematic flow diagram of an embodiment of a method according to the present disclosure.

With reference to FIG. 1, an embodiment of a method of controlling the adaptive HTTP streaming of media content between a HTTP server node and a HTTP client node in a communication system will be described. As mentioned before, the media content e.g. video, audio etc is arranged as a plurality of periods, each of which comprises a plurality of representations or versions of media segments. Initially, temporal alignment information is provided S10 for the media segments of each representation. This temporal alignment information provides indications of the temporal relation between the segments within each of the plurality of representations of the same media content. In other words, the temporal alignment information provides information about e.g. which segment of which representation starts at a given point in time, duration of each respective segment, whether several representations of the same segment are temporally aligned or not etc. Further, key frame location information is provided S20 for the media segments. The key frame location information provides indications about the location of key frames in the media segments. Both types of information can be provided explicitly or implicitly, which will be illustrated by a few examples further down.

Finally, the adaptivity of the HTTP streaming session is controlled based on at least one of the provided temporal alignment information and the key frame location information.

Figure 2:
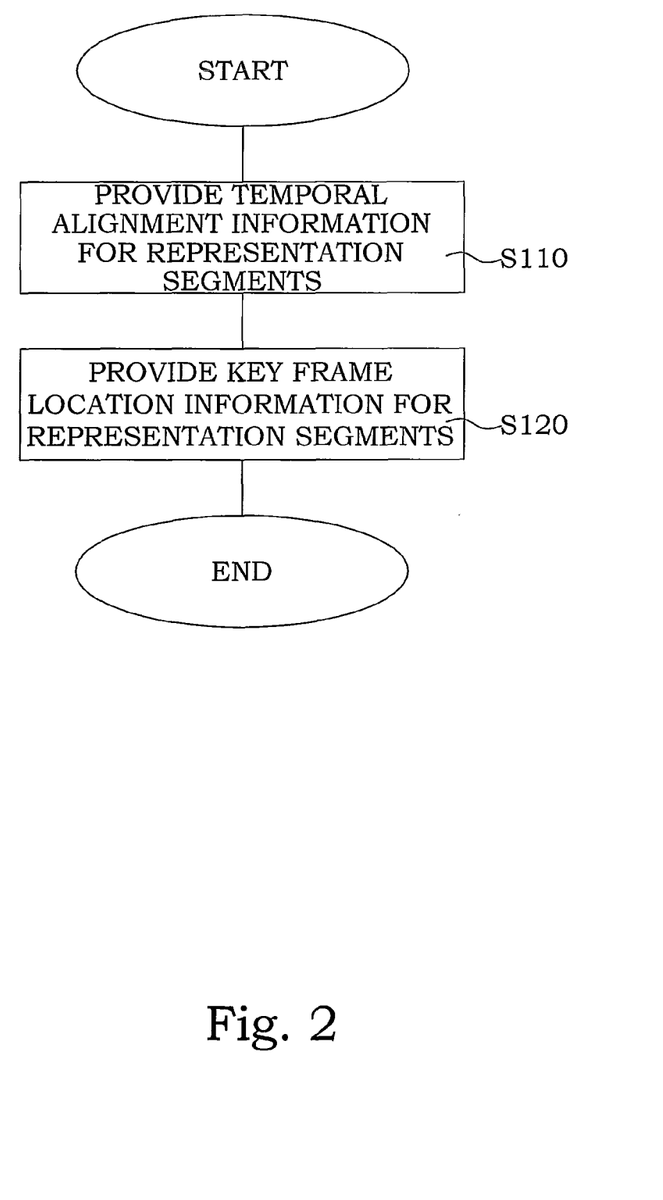
FIG. 2 is a schematic flow diagram of an embodiment of a method for use in a HTTP streaming server node according to the present disclosure.

An embodiment of a method in a HTTP streaming server node will be described below, with reference to FIG. 2.

In a HTTP streaming server node media content to be transmitted is segmented prior to transmission, in addition a plurality of versions or representations of one or more segments are provided for streaming to a client node. The server node may choose, depending on factors such as client friendliness, to segment (or receive pre-coded segments) each representation at exactly the same point. In this case, all segments are temporally aligned. In case the server node decides to segment the representations at differing points, e.g. for cache friendliness, some segments may be temporally aligned whereas others are un-aligned. In order to aid the adaptivity at a receiving client node, the server node needs to signal how the representations are (or are not) temporally aligned. Consequently, the server node provides S110 temporal alignment information for the segments of the respective representations to the receiving client node. In addition, the server node selects or decides on if and where to include any key frames in the various representation segments. This selection is performed, in correspondence with the temporal alignment strategy, based on a tradeoff between client friendliness and the ability to take generic pre-coded content. Based on the chosen key frame strategy, the server node additionally provides S120 key frame location information for the various segments and representations to the receiving client node.

The steps of providing the temporal alignment information S110 and the key frame location information S120 can be performed implicitly or directly. By providing information indicating that all segments have equal duration, it is possible to conclude that all segments of all representations are temporally aligned. For example, a default value may be specified.

According to a particular embodiment, the above mentioned temporal alignment information and key frame location information are signaled to the receiving client node in the manifest file or media presentation description which is provided to the receiving client node. However, although not as beneficial, the information can be provided to the client node through some other exchange of information.

Particularly, the key frame location information can include signaling in the manifest whether all or some particular, segments start with a key frame(s). This can be done by, for example, using a flag, StartsWithRAP. Since starting with a key frame makes adaptivity simpler, the client can then choose to only provide adaptivity in case this flag signals that specific segment starts with a key frame.

The abovementioned signaling may be either implicit or explicit. For example, a default value may be specified.

Instead of explicitly signaling that a key frame or random access point is present in the beginning of the segment, or where it is in the beginning of the segment, a signaling may be provided describing the RAP or GOP structure of the stream. In this way, the client can calculate where in the stream the key frames are.

The term temporally aligned segments is used above. The present disclosure applies equally well to constant segment durations (which may or may not coincide with temporally aligned segments). For example, it may be signaled that there is temporal alignment on every third audio packet.

Figure 3:
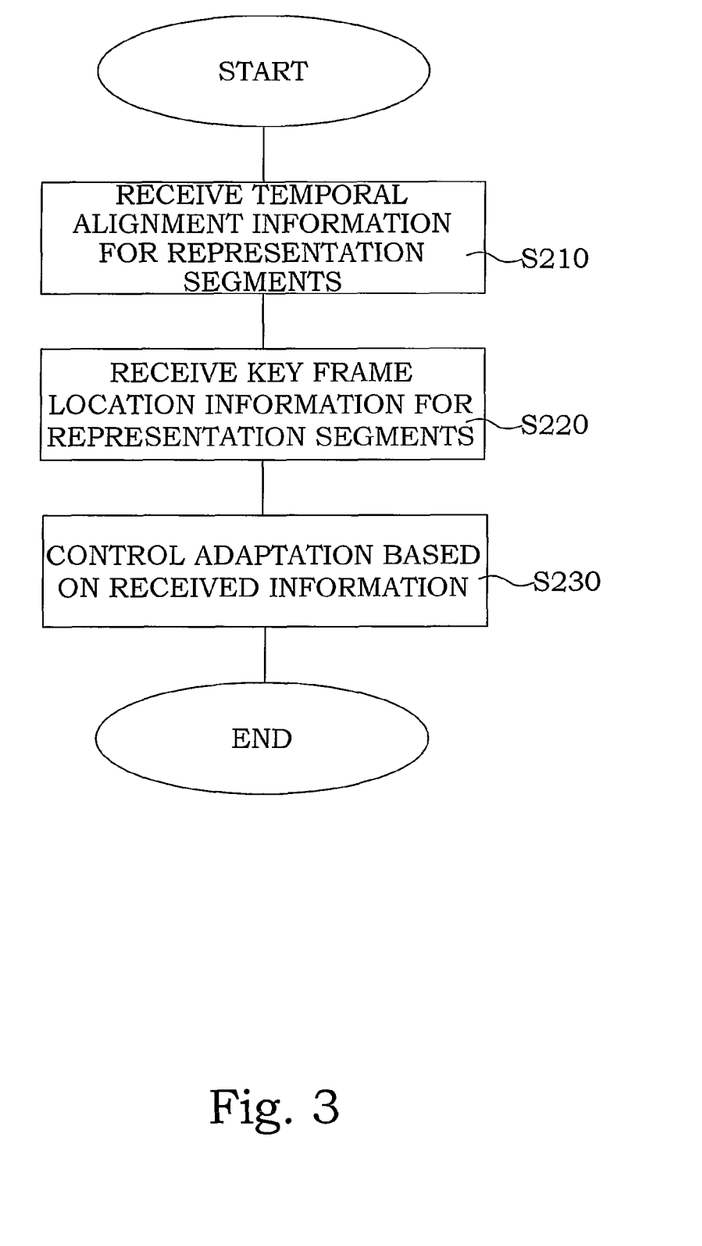
FIG. 3 is a schematic flow diagram of an embodiment of a method for use in a HTTP streaming client node according to the present disclosure.

Embodiments of a method in a HTTP streaming client node e.g. receiving client node will be described below with reference to FIG. 3.

A client node takes part in a HTTP streaming session from a HTTP streaming server node. The client node receives S210 information about the temporal alignment (or lack thereof) for some or all of the available representations and their respective segments. In addition, the client node receives S220 information on the location of key frames in the representation segments. Based on the received information, client node can then S230 control its adaptivity for the streaming session by performing adaptation depending on whether or not temporally aligned segments are signaled and whether or not segments start with a key frame.

If the client receives information that the segments of the representations are temporally aligned, it may adapt directly on a segment border without needing to recalculate the timeline of the new representations. In contrast, if the client receives information that the segments are not temporally aligned, the client needs further information (e.g. from inside the file or from the beginning of the presentation) supporting the synchronization of these streams and then performing splicing of media.

Some embodiments illustrating the control of the adaptivity based on the provided temporal alignment information will be discussed below. The client node can, according to one embodiment, chose to perform adaptation only if temporally aligned segments are indicated, either explicitly or implicitly by receiving and indication that all segments have equal duration. Further, the client can, according to a further embodiment, chose to perform adaptation only if both temporal alignment and constant segment duration have been indicated According to a further embodiment, the client performs adaptation by concatenating encoded segments when temporally-aligned segments are signaled and the codec data is the same.

In addition constant segment duration signaling can help client perform special playback trick, for instance, fast forward by skipping every second segment.

Upon reception of key-frame location information or key frame signaling, the client can decide whether it needs to download multiple segments simultaneously to provide uninterrupted playback. If the signaling shows the key-frame information, the client knows exactly at what point it can correctly decode the new representation. It may use this information to decide where to stop decoding the current stream before the switch.

Secondly, a client can use the lack of presence of key-frames at the beginning of a segment to decide not to allow adaptation to those segments (or representations).

A third possibility is to combine signaling of temporally aligned segments with signaled key-frames. If segments are both temporally aligned, and they start with a key frame, stream switching is most straight-forward, and the client can choose to do stream switching only if some specific combinations of the two signals are detected.

Another type of adaptivity may come into play when it applies to stereoscopic video. Depending on network bandwidth condition, one can adapt between stereo mode (download both left eye representation and right eye representation) or single mode (download only left/right eye representation). With the key frame signaling, the client can decide optimal ways to carry out adaptation. For example, if all segments of left eye representation start with key frame and quite few segments of right eye representation start with key frame, it would be desirable to adapt between stereo mode and right eye mode since frequent appearances of a key frame in left eye video allow flexibly stop and restart. This could largely facilitate tune in and tune out stereo mode as one wish.

Figure 4:
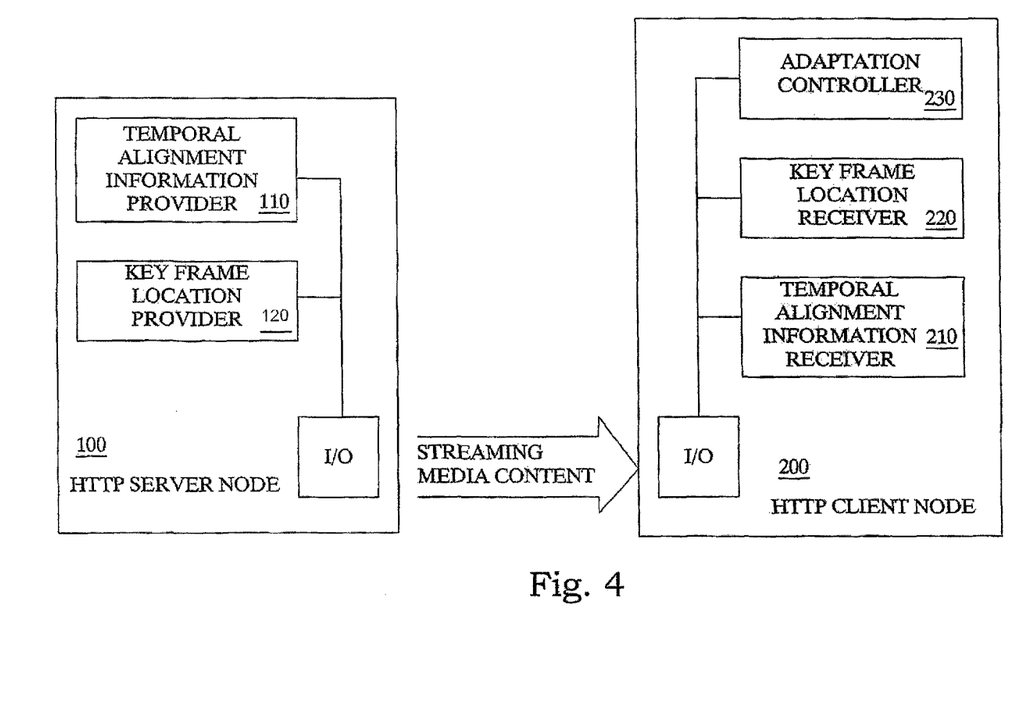
FIG. 4 is a schematic illustration of embodiments of a HTTP streaming server node and a HTTP streaming client according to the present disclosure.

A few embodiments of a system including at least one HTTP streaming server node 100 and at least one HTTP streaming client node 200 will be described with reference to FIG. 4. As indicated by the arrow marked STREAMING MEDIA CONTENT connecting the server node 100 and the client node 200, the two units are involved in a streaming session, wherein the client node 100 is fetching the content of a certain representation from the server node.

The HTTP streaming server node 100 includes a generic input/output unit I/O, and a temporal alignment information provider 110 for providing temporal alignment information (explicitly or implicitly) for the representation segments of an ongoing or initiated HTTP streaming session to the HTTP streaming client node 200. In addition, the server node 100 includes a key frame location information provider 120 for providing key frame location information for the representation segments. The HTTP streaming node 100 is preferably configured to include both the information elements into the manifest or media presentation description file for the current streaming session between the server node 100 and the client node 200. In addition to the above features, the server node 100 includes units for segmenting the representations. Finally, the server node includes all necessary (but not shown) units for initiating and upholding the HTTP streaming session.

The HTTP streaming client node 200 includes a generic input/output unit I/O, and a temporal alignment information receiver 210. The temporal alignment information receiver 210 is configured to receive information about the temporal alignment (explicitly or implicitly) of the representation segments of the streaming media from the HTTP streaming server node 100. The information can be received in the aforementioned manifest file, or by some other means in a separate information exchange. Further, the client node 200 includes a key frame location information receiver 220, for receiving information the location of any key frames in the various representation segments in the current streaming session. This can also be received in the aforementioned manifest file. Finally, the client node 200 includes an adaptation controller 230 for controlling the adaptation of the streaming session based on the one or both of the received temporal alignment information and key frame location information.

A few examples of different situations with varying temporal alignment will be described with reference to FIG. 5A-E. As examples of different representations, three levels of quality are indicated, namely high, medium and low.

Figure 5A:
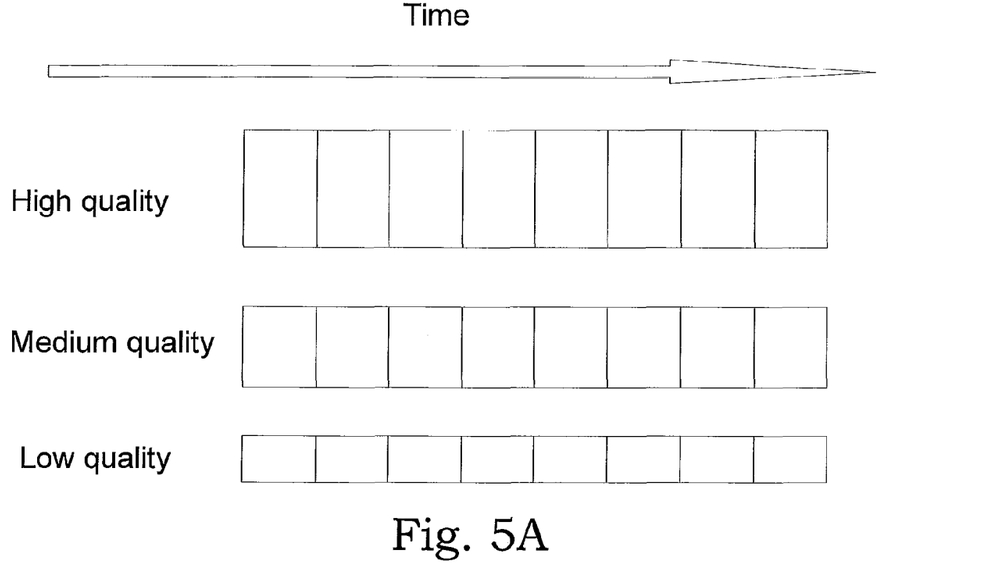

In FIG. 5A, all 8 segments of all versions or representations have the same duration, i.e. all the segments of each quality have the same duration. In other words, the streaming server has segmented the media with equal segment duration for all representations. The streaming server node then provides this information to the client node, preferably in the manifest at the beginning of the session. Consequently, the temporal alignment information indicates that all segments of all versions have the same duration and the client can control adaptation i.e. representation switch, to performed at any segment border.

Figure 5B:
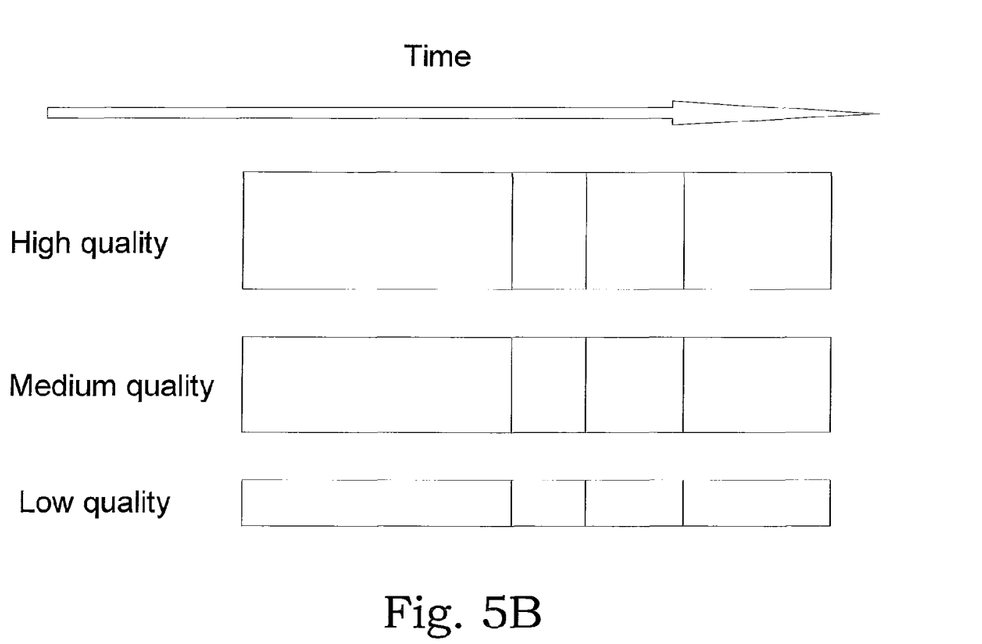

In FIG. 5B, all segments of all versions have aligned segment start points, i.e. the segments are temporally aligned. However, the first segment of each representation is longer than the second segment of each representation, but has the same duration for all the representations. In other words, the streaming server has segmented the media with temporal alignment but non-equal segment duration within each representation. Consequently, the temporal alignment information provides indications about the aligned starting points and the individual segment duration. As for the previous example, the client node can control adaptation to be performed at any segment start point since all segments of the three representations are temporally aligned.

Figure 5C:
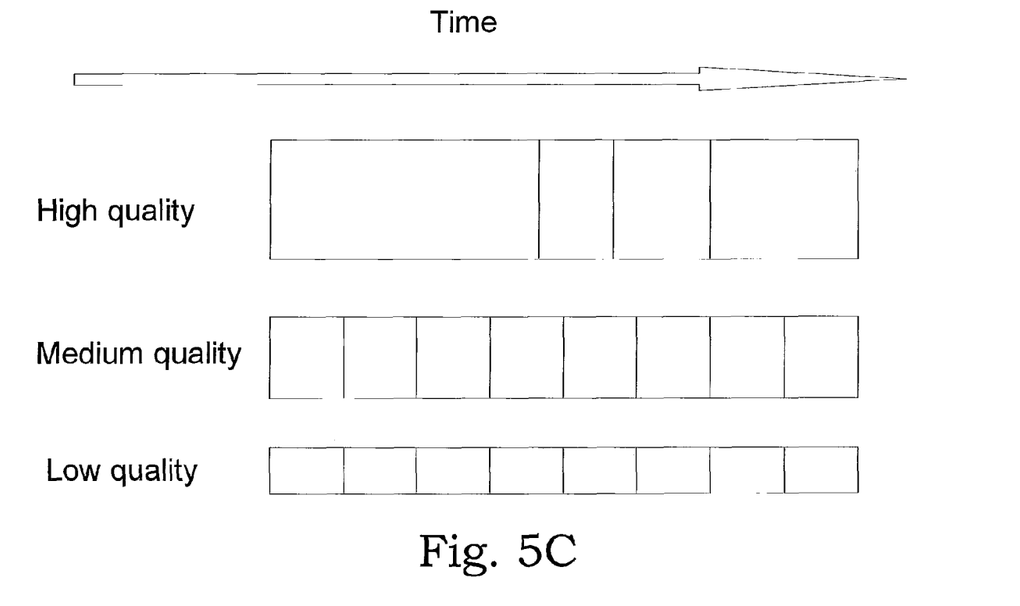

In FIG. 5C, all segments of two (or more) versions have the same duration. Here the medium and low quality versions are temporally aligned, but also have the same duration for all the segments, whereas the high quality representation segments have a varying duration. Consequently, the temporal alignment information indicates that the medium and low quality segments are temporally aligned, but the high quality representation is not. Therefore, adaptation can be controlled to be performed between all segment borders between the low and medium representation but not the high quality representation, where additional considerations or information needs to be used to enable adaptivity.

Figure 5D:
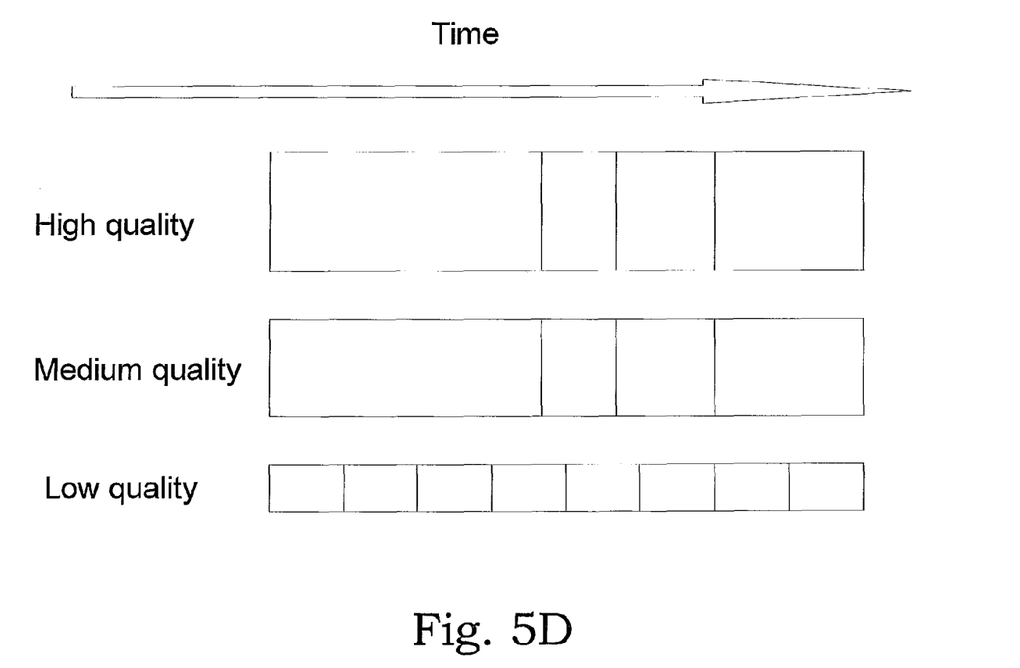

In FIG. 5D, all segments of two or more versions have aligning segment start points. This is similar to the case in FIG. 5C, but the duration of segments at the same quality are not constant. In this example, the temporal alignment information indicates that the high and medium quality representations are temporally aligned and have varying segment durations. As understood from the FIG. 5C, a client node can then control adaptivity to be performed at segment borders for the high and medium quality representations but not the low quality one.

Figure 5E:
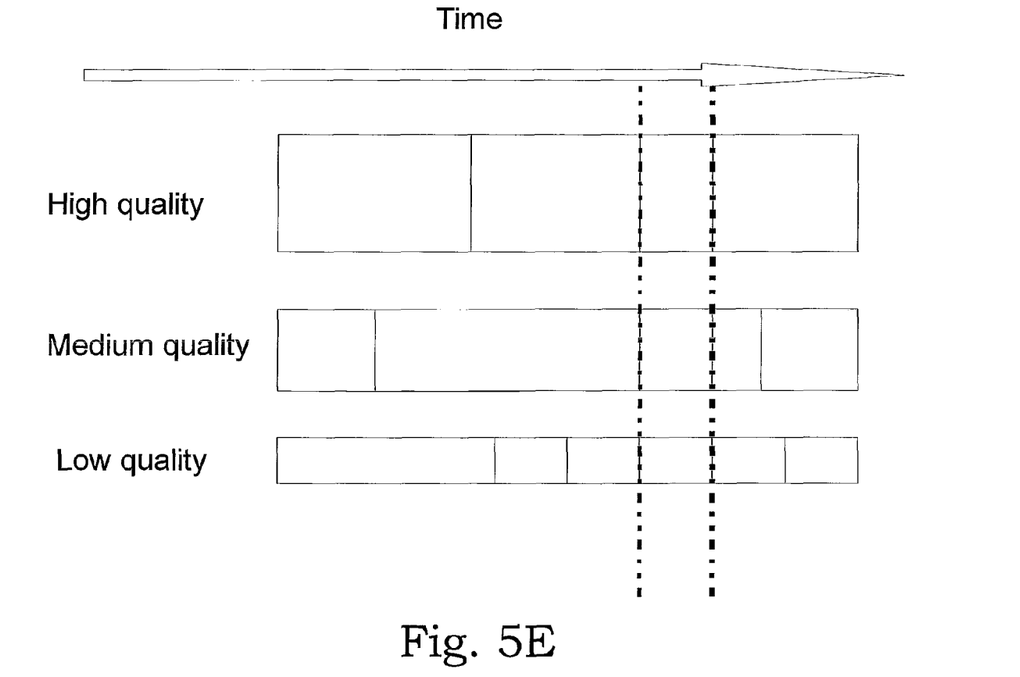

Finally, in FIG. 5E, there is temporal alignment between one or more segment boundaries of two or more versions (as indicated by the dashed vertical lines), at one or more points in time. This is a more general case, where some specific points in time are made more appropriate for quality switching. In this case, the temporal alignment information indicates which segment boundaries of which representations that are temporally aligned. As shown by the example, all three representations are temporally aligned at the indicated segment boundaries, wherefore it is possible to control adaptivity between all quality representations at these specific points in time, but not at other points in time.

A few illustrative examples relating to key frame location information will be provided below with reference to FIG. 6A-D. As mentioned before, the streaming server can provide information about the key frame location to indicate if all or some particular segment starts with a key frame. In response, a client node can chose to provide adaptivity in case a specific segment starts with a key frame, or some other criteria.

Figure 6A:
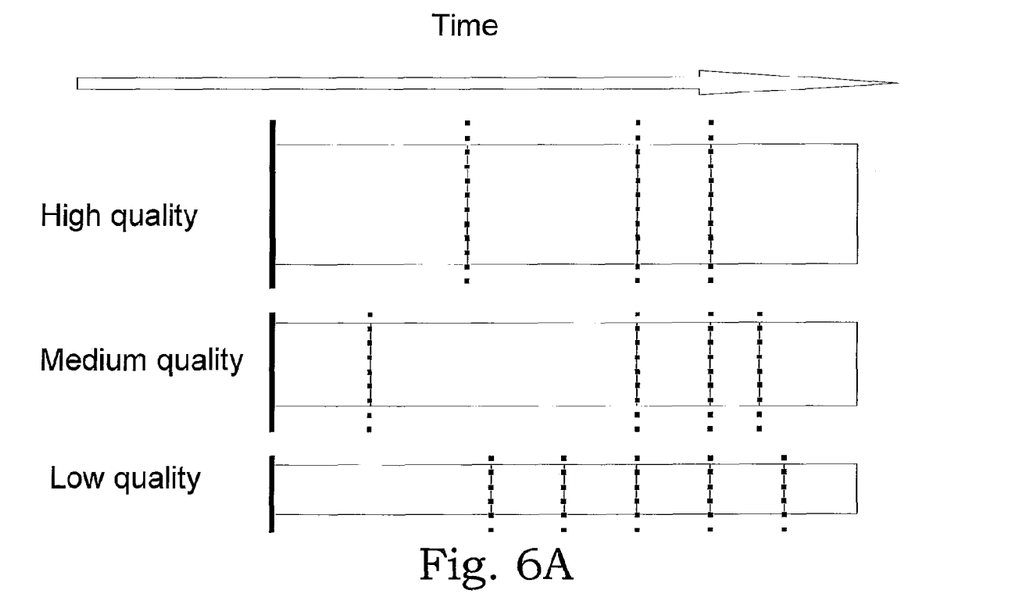

In FIG. 6A, all segments of all versions start with a key frame (as indicated by the dashed vertical lines). The information of the key frame location is then provided to the client node, and the client node can chose to provide adaptivity e.g. switch representation at any segment of any representation.

Figure 6B:
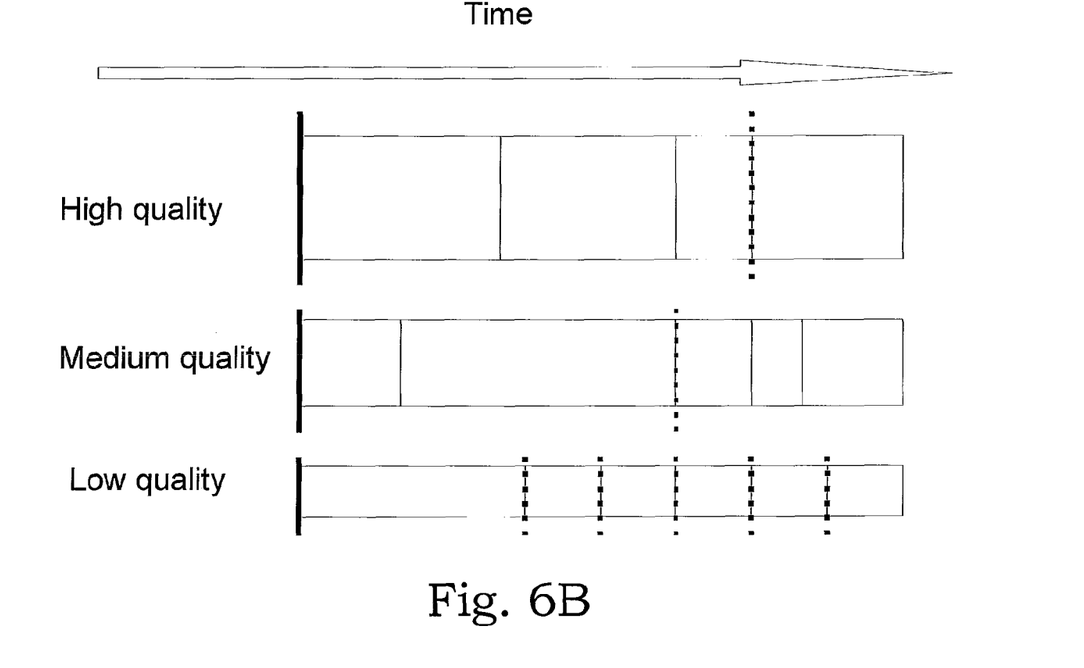

In FIG. 6B, all segments of one version start with a key frame. In this case, only the low quality version has a key frame in all segments, whereas the medium and high quality versions have one key frame in one segment each. Consequently, it is only possible to control adaptation to be performed between the low and medium quality at one particular segment at one point in time, and between the low and high quality at another particular segment at another later point in time.

Figure 6C:
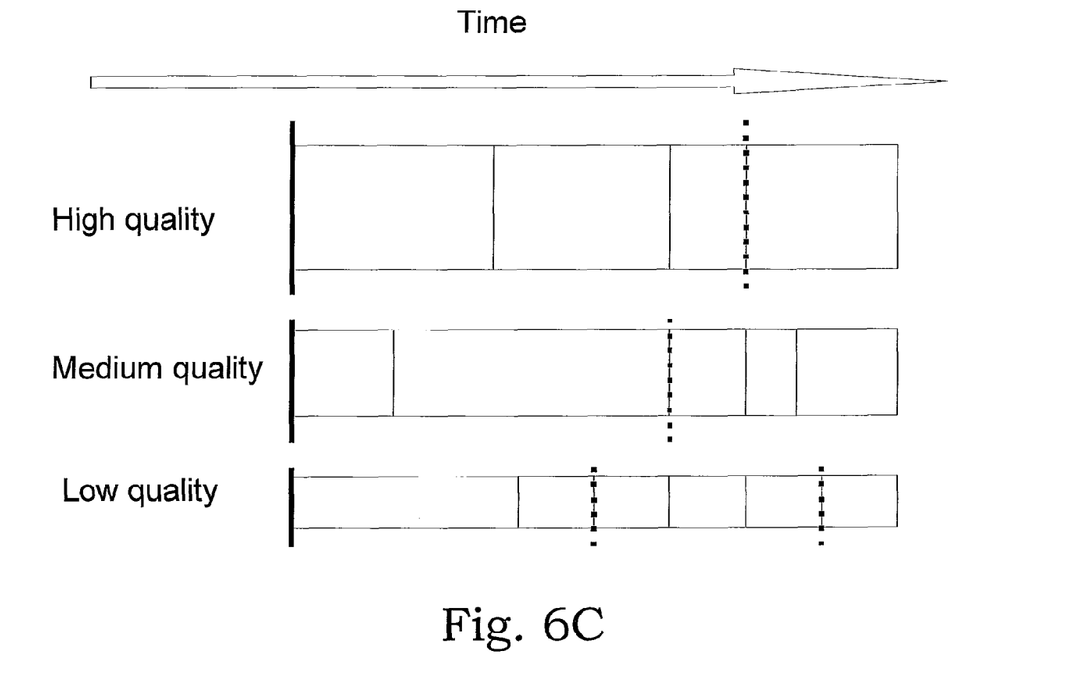

In FIG. 6C, one or more segments of one or more versions start with a key frame. This is signaled to the client node, which then can chose to provide adaptivity based on those provided key frames.

Figure 6D:
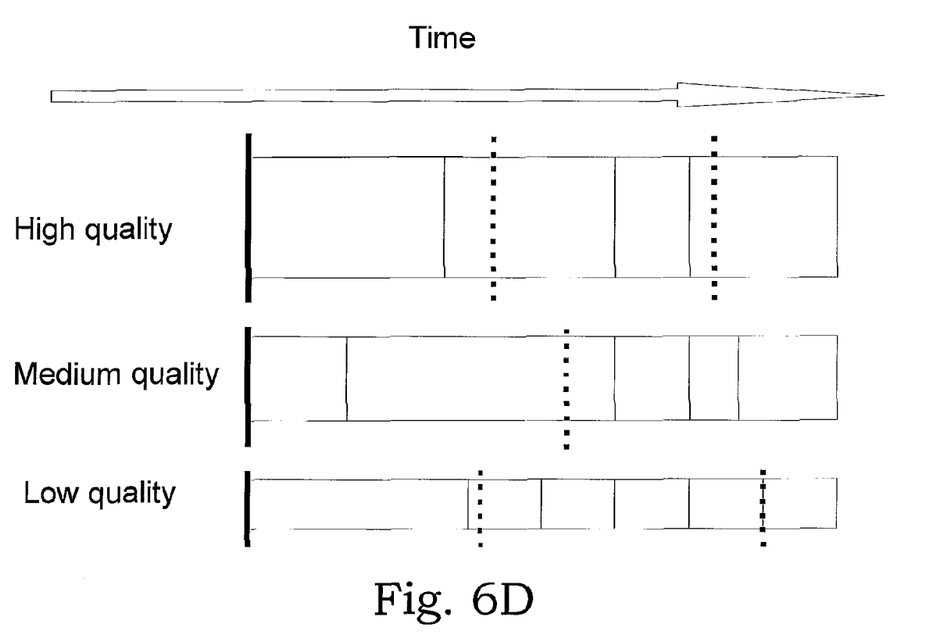

Finally, in FIG. 6D, the location of one or more key frames in one or more segments are provided and received in the receiving client node. In contrast to the previous embodiments, these key frames are not provided at the start of their respective segments, but rather contain within their segments.

The steps, functions, procedures, and/or blocks described above may be implemented in hardware using any conventional technology, such as discrete circuit or integrated circuit technology, including both general-purpose electronic circuitry and application-specific circuitry.

Alternatively, at least some of the steps, functions, procedures, and/or blocks described above may be implemented in software for execution by a suitable processing device, such as a microprocessor, Digital Signal Processor (DSP) and/or any suitable programmable logic device, such as a Field Programmable Gate Array (FPGA) device.

It should also be understood that it might be possible to re-use the general processing capabilities of the network nodes. For example this may, be performed by reprogramming of the existing software or by adding new software components.

The software may be realized as a computer program product, which is normally carried on a computer-readable medium. The software may thus be loaded into the operating memory of a computer for execution by the processor of the computer. The computer/processor does not have to be dedicated to only execute the above-described steps, functions, procedures, and/or blocks, but may also execute other software tasks.

Figure 7:
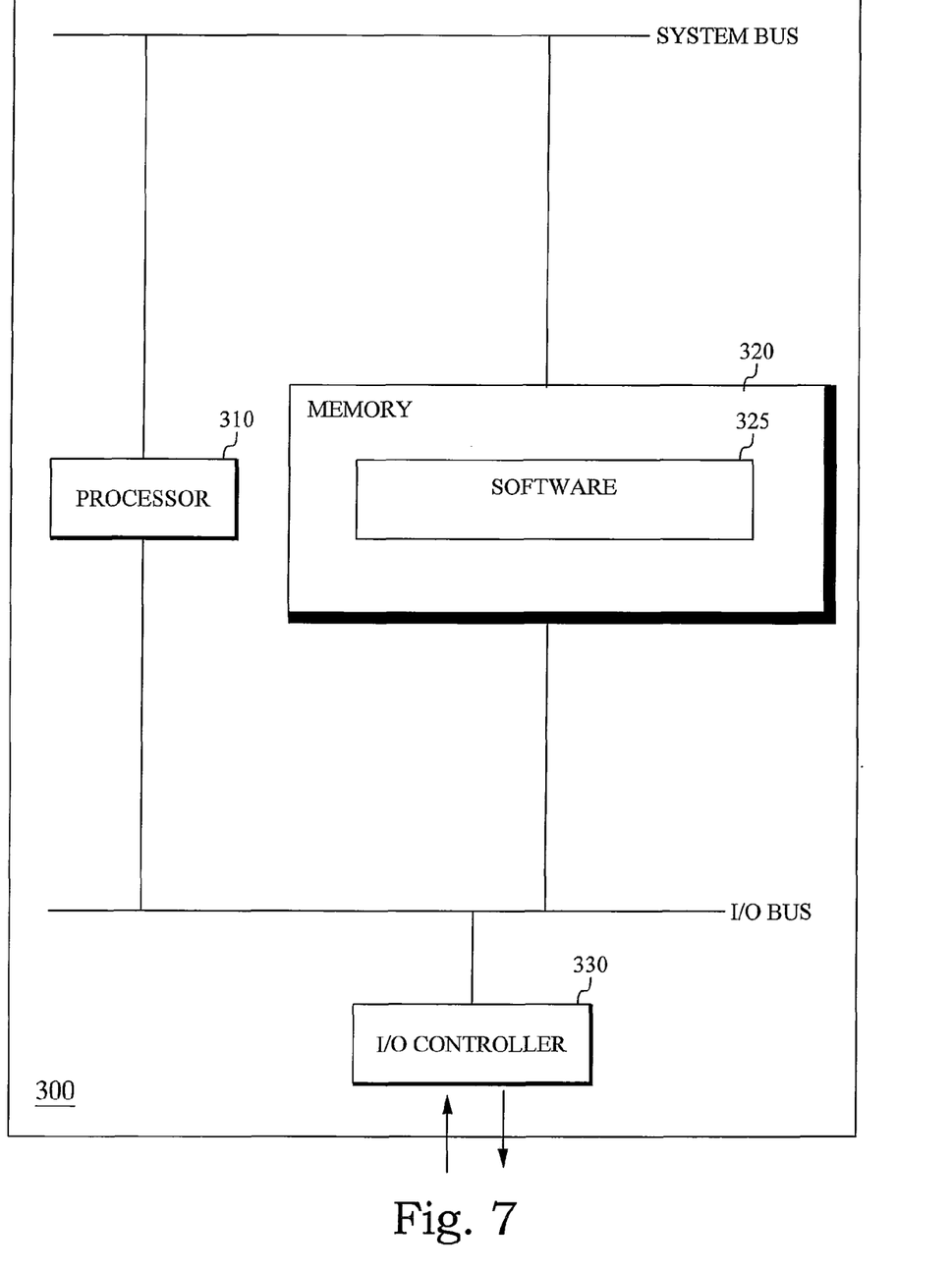
FIG. 7 is a schematic illustration of an implementation of the present disclosure.

In the following, an example of a computer-implementation will be described with reference to FIG. 7. A computer 300 comprises a processor 310, an operating memory 320, and an input/output unit 330. In this particular example, at least some of the steps, functions, procedures, and/or blocks described above are implemented in software 325, which is loaded into the operating memory 320 for execution by the processor 310. The processor 310 and memory 320 are interconnected to each other via a system bus to enable normal software execution. The I/O unit 330 may be interconnected to the processor 310 and/or the memory 320 via an I/O bus to enable input and/or output of relevant data such as input parameter(s) and/or resulting output parameter(s).

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of controlling adaptive HTTP streaming of media content between an HTTP server and an HTTP client in a communication system, the media content being arranged as a plurality of periods, each period comprising a plurality of representations of three or more media segments, the method comprising:
   providing temporal alignment information for the media segments of the plurality of representations, the temporal alignment information providing indications about a temporal relation common to all of the segments of the plurality of representations of the media content, wherein providing the temporal alignment information implicitly comprises:
      providing a segment duration for at least one segment of at least one of the plurality of representations; and
      providing an indication that the plurality of representations share a common starting time;
   providing key frame location information for the media segments, the key frame location information indicating whether a key frame is located at a start of each segment of the plurality of representations, wherein the key frame location information indicates a key frame located in at least one segment of at least one representation; and
   controlling adaptation of the HTTP streaming of the media content based on at least one of the provided temporal alignment information and the provided key frame location information.

2. The method of claim 1, wherein controlling adaptation of the HTTP streaming comprises controlling adaptation of the HTTP streaming based on both of the provided temporal alignment information and the provided key frame location information.

3. The method of claim 1, wherein controlling adaptation of the HTTP streaming comprises controlling adaptation of the HTTP streaming directly at a segment border if the temporal alignment information indicates that a start of at least one respective segment of at least two of the plurality of representations are temporally aligned.

4. The method of claim 1, wherein controlling adaptation of the HTTP streaming comprises controlling adaptation of the HTTP streaming if constant segment duration is provided.

5. The method of claim 1, wherein providing the key frame location information comprises providing the key frame location information directly or implicitly.

6. A method for use in an HTTP server node for streaming of media content to an HTTP client in a communication system, the media content being arranged as a plurality of periods, each period comprising a plurality of representations of three or more media segments, the method comprising:
   providing temporal alignment information for the media segments of the plurality of representations, the temporal alignment information providing indications about a temporal relation common to all of the segments of the plurality of representations of the media content, wherein providing the temporal alignment information implicitly comprises:
      providing a segment duration for at least one segment of at least one of the plurality of representations; and
      providing an indication that the plurality of representations share a common starting time; and
   providing key frame location information for the media segments, the key frame location information indicating whether a key frame is located at a start of each segment of the plurality of representations, wherein the key frame location information indicates a key frame located in at least one segment of at least one representation.

7. The method of claim 6, wherein providing the temporal alignment information and the key frame location information comprises providing the temporal alignment information and the key frame location information in a media presentation description file or manifest file.

8. The method of claim 6:
   further comprising segmenting each of the plurality of representations at a common point in time:
   wherein providing the temporal alignment information comprises providing the temporal alignment information indicating that all of the plurality of representations are temporally aligned at the common point in time.

9. The method of claim 6:
   further comprising segmenting each of the plurality of representations at the key frame position.

10. The method of claim 6:
    further comprising segmenting each of the plurality of representations at different points in time;
    wherein providing temporal alignment information comprises providing temporal alignment information indicating that the plurality of representations lack temporally aligned segments.

11. The method of claim 6:
    further comprising segmenting each of the plurality of representations at non-key frame positions;
    wherein providing key frame location information comprises providing key frame location information indicating key frame positions segmented into the plurality of representations.

12. A method in an HTTP client node for receiving streaming media content from an HTTP server node in a communication system, the media content being arranged as a plurality of periods, each period comprising a plurality of representations of three or more media segments, the method comprising:
    receiving temporal alignment information for the media segments of the plurality of representations, the temporal alignment information providing indications about a temporal relation common to all of the segments of the plurality of representations of the media content, wherein receiving the temporal alignment information implicitly comprises:
       receiving a segment duration for at least one segment of at least one of the plurality of representations; and
       receiving an indication that the plurality of representations share a common starting time;
    receiving key frame location information for the media segments, the key frame location information indicating whether a key frame is located at a start of each segment of the plurality of representations, wherein the key frame location information indicates a key frame located in at least one segment of at least one representation; and controlling adaptation of the HTTP streaming of the media content based on at least one of the received temporal alignment information and the received key frame location information.

13. The method of claim 12, wherein controlling adaptation of the HTTP streaming comprises controlling adaptation of the HTTP streaming if the temporal alignment information indicates that temporally aligned segments are provided.

14. The method of claim 13, wherein controlling adaptation of the HTTP streaming comprises controlling adaptation of the HTTP streaming if the temporal alignment information is received implicitly by a constant segment duration indication.

15. The method of claim 14, wherein controlling adaptation of the HTTP streaming comprises controlling adaptation of the HTTP streaming if both explicit temporal alignment information and the constant segment duration indication are received.

16. The method of claim 12, wherein controlling adaptation of the HTTP streaming comprises controlling adaptation of the HTTP streaming by concatenating encoded segments if temporally alignment information is received and the codec data is the same.

17. The method of claim 12, wherein controlling adaptation of the HTTP streaming comprises controlling adaptation of the HTTP streaming only if key frame location indications are received.

18. An HTTP server node for streaming of media content to an HTTP client in a communication system, the media content being arranged as a plurality of periods, each period comprising a plurality of representations of three or more media segments, the server node comprising:

a temporal alignment information provider circuit configured to provide temporal alignment information for the media segments of the plurality of representations, the temporal alignment information providing indications about a temporal relation common to all of the segments of the plurality of representations of the media content, wherein the temporal alignment information provider circuit provides the temporal alignment information implicitly by:

providing a segment duration for at least one segment of at least one of the plurality of representations; and providing an indication that the plurality of representations share a common starting time; and a key frame location provider circuit configured to provide key frame location information for the media segments, the key frame location information indicating whether a key frame is located at a start of each segment of the plurality of representations, wherein the key frame location information indicates a key frame located in at least one segment of at least one representation.

19. An HTTP client node for receiving streaming of media content from an HTTP server node, the media content being arranged as a plurality of periods, each period comprising a plurality of representations of three or more media segments, the client node comprising:

a temporal alignment information receiver configured to receive temporal alignment information for the media segments of the plurality of representations, the temporal alignment information providing indications about a temporal relation common to all of the segments of the plurality of representations of the media content, wherein the temporal alignment information receiver receives the temporal alignment information implicitly by:

receiving a segment duration for at least one segment of at least one of the plurality of representations; and receiving an indication that the plurality of representations share a common starting time;

a key frame location receiver circuit configured to receive key frame location information for the media segments, the key frame location information indicating whether a key frame is located at a start of each segment of the plurality of representations, wherein the key frame location information indicates a key frame located in at least one segment of at least one representation; and an adaptation controller circuit configured to control adaptation of the HTTP streaming of the media content based on at least one of the received temporal alignment information and the received key frame location information.

* * * * *